United States Patent [19]

Kawata et al.

[11] 4,412,986

[45] Nov. 1, 1983

[54] NIFEDIPINE-CONTAINING SOLID PREPARATION COMPOSITION

[75] Inventors: Hiroitsu Kawata, Kawagoe; Tadayoshi Ohmura, Niiza; Katsuhiko Yano, Omiya; Mikio Matsumura, Tokyo; Saburo Higuchi, Hasuda; Yoshiaki Soeishi, Tokyo, all of Japan

[73] Assignee: Yamanouchi Pharmaceutical Co. Ltd., Tokyo, Japan

[21] Appl. No.: 254,882

[22] Filed: Apr. 16, 1981

Related U.S. Application Data

[62] Division of Ser. No. 908,510, May 22, 1978, abandoned.

[30] Foreign Application Priority Data

Jun. 7, 1977 [JP] Japan .................................. 52-67039
Jul. 14, 1977 [JP] Japan .................................. 52-84372

[51] Int. Cl.³ .................. A61K 31/79; A61K 31/455; A61K 47/00
[52] U.S. Cl. ..................................... 424/80; 424/266; 424/362
[58] Field of Search ......................... 424/266, 80, 362

[56] References Cited

U.S. PATENT DOCUMENTS

| | | | |
|---|---|---|---|
| 3,784,684 | 1/1974 | Bossert et al. | 424/266 |
| 3,799,934 | 3/1974 | Meyer et al. | 424/266 |
| 3,862,161 | 1/1975 | Bossert et al. | 424/266 |
| 3,920,823 | 11/1975 | Meyer et al. | 424/266 |
| 3,932,645 | 1/1976 | Meyer et al. | 424/266 |
| 3,943,140 | 3/1976 | Bossert et al. | 424/266 |
| 3,959,296 | 5/1976 | Bossert et al. | 424/266 |
| 3,971,796 | 7/1976 | Bossert et al. | 424/266 |

FOREIGN PATENT DOCUMENTS 1456618 11/1976 United Kingdom .

*Primary Examiner*—Douglas W. Robinson
*Attorney, Agent, or Firm*—Sprung, Horn, Kramer & Woods

[57] ABSTRACT

A novel nifedipine-containing solid pharmaceutical preparation composition comprising a mixture of nifedipine and at least one 1st(a) substance selected from polyvinyl pyrrolidone, methyl cellulose, hydroxypropyl cellulose and hydroxypropylmethyl cellulose; a mixture of nifedipine, at least one 1st(b) substance selected from polyvinyl pyrrolidone, urea, citric acid mannitol, succinic acid, methyl cellulose, hydroxypropyl cellulose, hydroxypropylmethyl cellulose and amino acid, and at least one 2nd substance selected from a surface active agent, polyethylene glycol, propylene glycol, glycerol, a glycerol fatty acid ester and a vegetable oil; or a mixture of nifedipine, the 1st(b) substance, the 2nd substance and calcium lactate.

The composition of this invention can increase the bioavailability of nifedipine and makes it possible to provide a nifedipine-containing pharmaceutical preparation which has small bulk and can be easily administered.

15 Claims, No Drawings

NIFEDIPINE-CONTAINING SOLID PREPARATION COMPOSITION

This is a division of application Ser. No. 908,510, filed May 22, 1978, now abandoned.

BACKGROUND OF THE INVENTION

1. Field of the Invention

The present invention relates to a solid composition of nifedipine (4-(2'-nitrophenyl)-2,6-dimethyl-3,5-dicarbomethoxy-1,4-dihydropyridine) and, more particularly, the invention relates to a novel nifedipine-containing solid composition having high bioavailability and small bulk for facilitating the administration thereof.

2. Description of the Prior Art

Nifedipine is a known material which possesses a coronary dilator activity and is useful for the treatment of so-called angina pectoris attack. Since it is difficult to foresee the occurrence of angina pectoris attack, the patient is sometimes forced to treat himself when an angina pectoris attack occurs and hence it is particularly desired that therapeutic substances of this kind used for the treatment of angina pectoris attack are pharmaceutical preparations capable of being easily administered as a matter of course and exhibiting a quick and certain effect. However, nifedipine exhibits low bioavailability by oral administration owing to the sparing solubility thereof and is liable to be decomposed by the action of light. Development of the aforesaid pharmaceutical preparations of nifedipine, therefore, has encountered great difficulty.

Hitherto, as the preparation of nifedipine for oral administration, there are known tablets, pills (U.K. Pat. No. 1,173,862), and oral-release capsules (U.S. Pat. No. 3,784,684). Among these preparations, the tablets and pills are reported to be less effective owing to the very slow absorbability (U.S. Pat. No. 3,784,684). On the other hand, the oral-release capsules are prepared by dissolving nifedipine using a solubilizing agent and filling the solution of nifedipine in a colored or shading capsule and hence exhibit their effect quickly and show good bioavailability. But since they are a liquid preparation, the forms of preparation are restricted and, in addition, the preparation step is very complicated as compared with the case of preparing solid preparations. Furthermore, since nifedipine is ordinally inferior in solubility, a large amount of solubilizers or solubilization aids is required for the preparation of such preparations for oral administration.

Therefore, the forms of these preparations inevitably become large and in case of commercially available liquid preparations (oral-release capsules), the weight of one capsule reaches 615 mg. In case of large tablets and capsules, specific forms such as ellipsoids and oblongs are employed for facilitating swallowing but even in such cases, they show resistance to swallowing if their weight is over 400 mg.

SUMMARY OF THE INVENTION

As the result of investigations on solid preparations of nifedipine under such circumstances, the inventors have discovered that a novel nifedipine-containing solid composition having the same high bioavailability and smaller bulk and capable of being more easily administered as compared with the aforesaid liquid preparations is obtained by compounding nifedipine with the specific substance or substances.

That is, according to this invention, there is provided a solid pharmaceutical composition of nifedipine comprising a a mixture of nifedipine and at least one substance selected from polyvinyl pyrrolidone, methyl cellulose, hydroxypropyl cellulose and hydroxypropylmethyl cellulose; (b) a mixture of nifedipine, at least one 1st substance selected from polyvinyl pyrrolidone, urea, citric acid, mannitol, succinic acid, methyl cellulose, hydroxypropyl cellulose, hydroxypropylmethyl cellulose and amino acid, and at least one 2nd substance selected from a surface active agent, polyethylene glycol, propylene glycol, glycerol, a glycerol fatty acid ester and a vegetable oil; or (c) a mixture of nifedipine, the 1st substance, the 2nd substance and calcium lactate.

The nifedipine-containing solid pharmaceutical composition of this invention may further contain, if necessary, coloring agents, sweetening agents, flavouring agents, and diluents.

DESCRIPTION OF THE PREFERRED EMBODIMENTS

Now, in one embodiment of this invention, an amino acid is used as one of the 1st substances and preferred examples of the amino acid are threonine, glycine, alanine, cysteine, lysine, and the like. In this case, the amino acid may be used in any of the D-form, L-form, and DL-form. Also, a surface active agent is employed as one of the 2nd substances and examples of the surface active agent are anionic surface active agents such as sodium alkylsulfate, etc., and nonionic surface active agents such as polyoxyethylene fatty acid ester, polyoxyethylene higher alcohol ether, polyoxyethylene castor oil derivatives a glycol fatty acid ester, etc., and they may be used alone or in mixtures thereof. Furthermore, the polyethylene glycol used as one of the 2nd substances in this invention is preferably a liquid substance such as PEG 200, PEG 400, PEG 600, etc. Also, as the preferred examples of the vegetable oils used as one of the 2nd substances, there are, for example, sesame oil, corn oil, soybean oil, rapeseed oil, olive oil and coconut oil.

Moreover, as the diluents which may be used together with the solid preparation composition of this invention, there are lactose, starch, crystalline cellulose, low-substituted hydroxypropyl cellulose, synthetic aluminum silicate, calcium hydrogenphosphate, anhydrous silicic acid, etc.

The solid composition of this invention may be produced in the following manner. That is, after dissolving nifedipine and at least one of the aforesaid substances in an organic solvent, or dissolving nifedipine together with at least one of the 1st substances and at least one of the 2nd substances in an organic solvent, or further dissolving or suspending nifedipine together with at least one of the 1st substances, at least one of the 2nd substances and calcium lactate in an organic solvent, or further adding, if necessary, coloring agents, sweetening agents, flavouring agents, and diluents to the solution or suspension, the organic solvent is removed in the usual manner such as by lyophilization, heating at normal pressure or under reduced pressure or spray drying, etc. Thus, a solid composition or a powdery solid composition is obtained.

The compounding ratio of nifedipine and each substance depends upon the kind of the substance but the compounding ratio of the substance or 1st substance to one part by weight of nifedipine is less than 20 parts by weight, preferably 1-10 parts by weight, that of the 2nd substance is 0.1-10 parts by weight, preferably 0.5-5 parts by weight, and that of calcium lactate is less than 20 parts by weight, preferably 1-10 parts by weight.

Any solvent which can dissolve nifedipine, the and the other substances can be used as the organic solvent for the production of the pharmaceutical preparation composition of this invention, and the solvent is used in an amount necessary for dissolving the components. Ordinarily, an organic solvent such as methanol, ethanol, chloroform, dichloromethane, etc., may be preferably used alone or as a mixture thereof in an amount of 5 parts by weight or more per one part by weight of nifedipine.

In the invention, the presence of the 2nd substance acts to increase synergistically the solubility of nifedipine for the 1st substance and thus contributes to decrease the compounding ratio of the 1st substance. Also, the addition of calcium lactate makes it possible to increase the compounding ratio of the liquid 2nd substance the amount of which must be restricted to a small amount for producing the solid composition without the presence of calcium lactate and hence contributes to further decrease the compounding ratio of the 1st substance. That is, in the case of adding calcium lactate, the necessary amount of the 1st substance is 1/5 to ½ of the amount thereof in the case of using no calcium lactate, which results in providing the preparation which is small and easily administered, the weight of one tablet or one capsule thereof being about 150-250 mg.

The property of the solid composition of this invention differs according to the substance or substances to be added but in any cases, a glassy or solid solution like material wherein nifedipine is dissolved in the 1st(a) substance or a mixture of the 1st substance and the 2nd substance is formed. Furthermore, when calcium lactate is added, it is considered that the aforesaid glassy or solid solution like material adsorbed on the calcium lactate particles is formed.

In the solid compositions of this invention, nifedipine is not easily decomposed and the compositions can be stored for a longer period of time than 3 years without causing separation of crystals.

The composition of this invention may be formed into powders, granules, tablets, capsules, pills, etc., in an ordinary manner. Also, in the case of using such tablets, powders, etc., the measurement, the production of packed powders, the administration, etc., can be easily practiced as compared with liquid preparations and the doses thereof can be properly increased or reduced.

Furthermore, since the addition of calcium lactate to the solid composition makes it very easy to pulverize the solid composition and improves remarkably the fluidity thereof, the solid composition containing calcium lactate is particularly suitable for producing a nifedipine-containing solid preparation for oral administration, such as tablets, powders, etc.

For proving the excellent bioavailability of the solid compositions of this invention, the change of the concentration of nifedipine in plasma with the passage of time in the case of orally administering the compositions will be described together with the experimental procedures.

Experiment I

Nifedipine was orally administered to male dogs (10.5-12.5 kg) which had been fasted for 16 hours in the form of preparation Ex.4, Ex.10 and the commercial capsules Adalat ® in a crossover design at a dose of 30 mg. The blood samples were obtained at 0.5, 1, 2, 4 and 7 hours after administration and the plasma concentration of the drug was determined by selected ion monitoring method as follows.

Deuterium labeled nifedipine aqueous solution (0.5 ml, 300 ng), 0.1 N HCl (2 ml) and 1% $NaNO_2$ (0.3 ml) were added to the plasma sample (1 ml), and the mixture was incubated at 45° for one hour, during which the 1,4-dihydropyridine ring of nifedipine was oxidized to the corresponding pyridine analogue. After cooling, the mixture was made alkaline with 2 N NaOH (0.5 ml) and extracted with benzene (4 ml). The organic layer was evaporated to dryness and ethylacetate (50 $\mu$l) was added to the residue. An aliquot of 1 $\mu$l was injected into the column of the gas chromatograph—mass spectrometer, and the amount of nifedipine in each sample was calculated by measuring the peak height ratio of the pyridine analogue of nifedipine (m/e 298) and deuterium labeled nifedipine (m/e 306) and referring to the standard curve.

|  | Plasma concentration of nifedipine (ng/ml) | | | | | AUC* |
| --- | --- | --- | --- | --- | --- | --- |
|  | 0.5 h | 1 h | 2 h | 4 h | 7 h | (ng · h/ml) |
| Ex. 4 (n = 2) | 189.8 | 176.0 | 70.3 | 35.5 | 12.2 | 439.2 |
| Adalat (n = 2) | 227.9 | 145.3 | 74.9 | 33.0 | 16.1 | 441.8 |

The values are the mean for 2 dogs.
*Area under the plasma concentration time curve.

| | Plasma concentration of nifedipine (ng/ml) | | | | | AUC* |
| --- | --- | --- | --- | --- | --- | --- |
| | 0.5 h | 1 h | 2 h | 4 h | 7 h | (ng · h/ml) |
| Ex. 10 (n = 3) | 187.5 ± 31.2 | 153.4 ± 32.2 | 70.9 ± 11.9 | 37.1 ± 12.3 | 10.8 ± 2.6 | 424.1 ± 62.7 |
| Adalat (n = 3) | 147.9 ± 44.1 | 112.8 ± 16.4 | 72.3 ± 14.5 | 26.4 ± 1.8 | 6.1 ± 3.1 | 342.3 ± 35.7 |

The values are the mean ± S.E. for 3 dogs.

Experiment II

Nifedipine was orally administered to 4 healthy male volunteers (53 to 70 kg, age 25 to 35), who had been fasted overnight, as the preparation Example 20 and as the commercial capsule Adalat ® in a crossover design at a dose of 10 mg. The blood samples were obtained at 0.5, 1, 2, 4 and 8 hours after administration and the plasma concentration of the drug was determined by selected ion monitoring method.

| | Plasma concentration of nifedipine (ng/ml) | | | | | AUC* (ng · h/ml) |
| --- | --- | --- | --- | --- | --- | --- |
| | 0.5 h | 1 h | 2 h | 4 h | 8 h | |
| Ex. 20 | 214 ± 11 | 138 ± 10 | 72 ± 6 | 29 ± 4 | 11 ± 2 | 427 ± 30 |
| Adalat | 152 ± 28 | 169 ± 24 | 75 ± 16 | 27 ± 5 | 7 ± 1 | 411 ± 43 |

The values are the mean ± S.E. for 4 volunteers.
*Area under the plasma concentration time curve.

Then, the process of producing the solid preparation composition of this invention will be practically explained by referring to the following examples.

EXAMPLE 1

After dissolving 1 g. of nifedipine and 10 g. of polyvinyl pyrrolidone in 50 g. of methanol, the solvent was distilled off from the solution by heating under normal pressure to provide a solid product.

EXAMPLE 2

After dissolving 1 g. of nifedipine and 5 g. of polyvinyl pyrrolidone in 20 g. of a mixture of methanol and carbon tetrachloride of 2:8 by weight ratio, the organic solvents were distilled off by spray dry method to provide a powdery product.

EXAMPLE 3

After dissolving 1 g. of nifedipine and 20 g. of polyvinyl pyrrolidone in 100 g. of methanol, the organic solvent was distilled off by lyophilization to provide a solid product.

EXAMPLE 4

After dissolving 1 g. of nifedipine, 2 g. of polyvinyl pyrrolidone, and 1 g. of sodium laurylsulfate in 60 g. of a mixture of chloroform and ethanol of 9:1 by weight ratio, the organic solvents were distilled off by spray dry method to provide a powdery product.

EXAMPLE 5

After dissolving 80 g. of dichloromethane and chloroform of 1:1 by weight ratio to 1 g. of nifedipine, 20 g. of polyvinyl pyrrolidone, 0.1 g. of polyoxyethylene (60) hydrogenated castor oil and 5 g. of polyethylene glycol 400, the solvents were distilled off by heating under reduced pressure to provide a solid product.

EXAMPLE 6

After dissolving 1 g. of nifedipine, 1 g. of polyethylene glycol 400 and 5 g. of polyvinyl pyrrolidone in 20 g. of methylene chloride, the solvent was distilled off by heating the solution under normal pressure to provide a solid product.

EXAMPLE 7

After dissolving 1 g. of nifedipine, 1 g. of sodium laurylsulfate, and 5 g. of polyvinyl pyrrolidone in 60 g. of a mixture of chloroform and ethanol of 9:1 by weight ratio and then uniformly dispersing 2.5 g. of calcium lactate in the solution, the solvents were distilled off from the dispersion by a spray dry method to provide a powdery product.

EXAMPLE 8

After dissolving 1 g. of nifedipine, 5 g. of polyethylene glycol 400 and 10 g. of polyvinyl pyrrolidone in 30 g. of dichloromethane and then uniformly dispersing 10 g. of calcium lactate in the solution, the organic solvent was distilled off from the dispersion by heating under normal pressure to provide a solid product. By pulverizing the solid product in a conventional manner, a powdery product was obtained.

EXAMPLE 9

After dissolving 1 g. of nifedipine, 1 g. of sesame oil, 5 g. of hydroxypropylmethyl cellulose, and 0.1 g. of polyoxyethylene (60) hydrogenated castor oil in 20 g. of a mixture of dichloromethane and methanol of 8:2 by weight ratio and then uniformly dispersing 5 g. of calcium lactate in the solution, the organic solvents were distilled off by heating the dispersion under reduced pressure to provide a solid product. By pulverizing the solid product in a conventional manner, a powdery product was obtained.

EXAMPLE 10

After dissolving 1 g. of nifedipine, 1 g. of polyethylene glycol 400, and 5 g. of polyvinyl pyrrolidone in 50 g. of dichloromethane and then uniformly dispersing 10 g. of calcium lactate to the solution, the organic solvent was distilled off by heating the dispersion under normal pressure to provide a solid product. By pulverizing the solid product in a conventional manner, a powdery product was obtained. To 17 g. of the powdery product thus obtained were added 2.8 g. of corn starch and 0.2 g. of magnesium stearate followed by mixing uniformly and 200 mg. of aliquots of the mixed powder were filled in size 2, hard gelatin capsules using a capsule filler.

EXAMPLE 11

After dissolving 1 g. of nifedipine, 0.5 g. of glycerol monooleic acid ester, and 10 g. of methyl cellulose in 70 g. of a mixture of dichloromethane and methanol of 7:3 by weight ratio and then uniformly dispersing 1 g. of calcium lactate in the solution, the organic solvents were distilled off by a spray dry method to provide a powdery product.

EXAMPLE 12

After dissolving 1 g. of nifedipine, 1 g. of glycerol, 3 g. of hydroxypropyl cellulose, and 5 g. of calcium lactate in 200 g. of methanol, the organic solvent was distilled off by lyophilization to provide a solid product. By pulverizing the solid product in a conventional manner, a powdery product was obtained.

EXAMPLE 13

After dissolving 1 g. of nifedipine, 2 g. of octyldecyl triglyceride, 5 g. of mannitol, and 10 g. of calcium lactate in 150 g. of methanol, the organic solvent was distilled off by heating the solution under normal pressure to provide a solid product. By pulverizing the solid product in a conventional manner, a powdery product was obtained.

EXAMPLE 14

After dissolving 1 g. of nifedipine, 1 g. of polyoxyethylene tridecyl ether, and 5 g. of urea in 20 g. of methanol and then uniformly dispersing 8 g. of calcium lactate in the solution, the organic solvent was distilled off by heating the dispersion under normal pressure to provide a solid product. By pulverizing the solid product in a conventional manner, a powdery product was obtained.

EXAMPLE 15

After dissolving 1 g. of nifedipine, 1 g. of corn oil, and 5 g. of L-threonine in 30 g. of methanol and then uniformly dispersing 10 g. of calcium lactate in the solution, the organic solvent was distilled off by heating the dispersion under reduced pressure to provide a solid product. By pulverizing the solid product in a conventional manner, a powdery product was obtained.

EXAMPLE 16

After dissolving 1 g. of nifedipine, 2 g. of propylene glycol, 2 g. of citric acid, and 5 g. of calcium lactate in 200 g. of methanol, the organic solvent was distilled off by lyophilization to provide a solid product. By pulverizing the solid product in a conventional manner, a powdery product was obtained.

EXAMPLE 17

After dissolving 1 g. of nifedipine, 5 g. of polyethylene glycol 400, and 5 g. of polyvinyl pyrrolidone in 150 g. of dichloromethane and then uniformly dispersing 10 g. of calcium lactate in the solution, the organic solvent was distilled off by a spray dry method to provide a powdery product.

EXAMPLE 18

After dissolving 1 g. of nifedipine, 1 g. of polyethylene glycol 400, 5 g. of hydroxypropylmethyl cellulose in 80 g. of a mixture of dichloromethane and methanol of 7:3 by weight ratio and then uniformly dispersing 5 g. of calcium lactate in the solution, the organic solvents were distilled off by a spray dry method to provide a fine-powdery product.

To 12 g. of the fine-powdery product thus obtained were added 1.8 g. of corn starch, 1 g. of calcium carboxymethyl cellulose, and 0.2 g. of magnesium stearate followed by mixing uniformly and from the mixture, tablets each having a weight of 150 mg. were produced using a flat faced punch of 8 mm. diameter.

EXAMPLE 19

After dissolving 1 g. of nifedipine, 1 g. of polyethylene glycol 400, and 5 g. of polyvinyl pyrrolidone in 30 g. of dichloromethane and then uniformly dispersing 5 g. of calcium lactate in the solution, the organic solvent was distilled off by a spray dry method to provide a fine-powdery product.

To 11 g. of the fine-powdery product thus obtained were added 8 g. of crystalline lactose 3.7 g. of calcium carboxymethyl cellulose, 0.1 g. of light anhydrous silicic acid, and 0.2 g. of magnesium stearate followed by mixing uniformly and from the mixture, tablets each having a weight of 230 mg. were produced using a flat faced punch of 8.5 mm. diameter.

EXAMPLE 20

After dissolving 10 g. of nifedipine, 10 g. of polyethylene glycol 400, and 50 g. of polyvinyl pyrrolidone in 300 g. of dichloromethane and then uniformly dispersing 50 g. of calcium lactate in the solution, 380 g. of lactose was granulated by a fluidized-bed granulating and drying method using the dispersion thus obtained to provide a granular powder.

EXAMPLE 21

After dissolving 1 g. of nifedipine, 1 g. of polyethylene glycol 400, and 5 g. of polyvinyl pyrrolidone in 30 g. of dichloromethane and uniformly dispersing 5 g. of synthetic aluminum silicate in the solution, the organic solvent was distilled off by a fluidized-bed granulating and drying method to provide a fine-powdery product.

What is claimed is:

1. A nifedipine-containing solid composition comprising a coprecipitate (a) of nifedipine and (b) about 1 to 20 times its weight of a member selected from the group consisting of polyvinylpyrrolidone, methylcellulose, hydroxypropylcellulose and hydroxypropylmethylcellulose.

2. A composition according to claim 1, wherein (b) is present in about 1 to 10 times the weight of (a).

3. A composition according to claim 1, wherein (b) is polyvinylpyrrolidone.

4. A composition according to claim 1, wherein (b) is methylcellulose.

5. A composition according to claim 1, wherein (b) is hydroxypropylcellulose.

6. A composition according to claim 1, wherein (b) is hydroxypropylmethylcellulose.

7. A composition according to claim 1, further containing (c) about 0.1 to 10 parts per part by weight of (a) of at least one compound selected from the group consisting of an anionic surface active agent, a nonionic surface active agent, polyethylene glycol, propylene glycol, glycerol, a glycerol fatty acid ester and a vegetable oil.

8. A composition according to claim 7, wherein (c) is sodium lauryl sulfate.

9. A composition according to claim 7, wherein (c) is polyethylene glycol.

10. A composition according to claim 1, further containing (d) about 0.1 to 10 parts per part by weight of (a) of at least one member selected from the group consisting of aluminum silicate and calcium lactate.

11. A method of effecting coronary vascular dilation with high bioavailability in humans and animals which comprises orally administering a therapeutically effective amount of the composition claimed in claim 1.

12. A method of effecting coronary vascular dilation with high bioavailability in humans and animals which comprises orally administering a therapeutically effective amount of the composition claimed in claim 7.

13. A method of effecting coronary vascular dilation with high bioavailability in humans and animals which comprises orally administering a therapeutically effective amount of the composition claimed in claim 11.

14. A composition according to claim 1 in the form of a tablet of less than 400 mg.

15. A composition according to claim 1 in the form of a tablet of less than 250 mg.

* * * * *

UNITED STATES PATENT AND TRADEMARK OFFICE
CERTIFICATE OF CORRECTION

PATENT NO. : 4,412,986

DATED : November 1, 1983

INVENTOR(S) : Hiroitsu Kawata et al.

It is certified that error appears in the above-identified patent and that said Letters Patent is hereby corrected as shown below:

1st page, After "No. 73 Assignee"   Delete "YAMANOUCHI PHARMACEUTICAL CO. LTD, Tokyo, Japan" and substitute --BAYER AG, Leverkusen, Federal Republic of Germany--

Signed and Sealed this

Seventeenth Day of September 1985

[SEAL]

Attest:

DONALD J. QUIGG

Attesting Officer

Commissioner of Patents and Trademarks—Designate